(12) United States Patent
Hoyte

(10) Patent No.: US 8,579,873 B2
(45) Date of Patent: Nov. 12, 2013

(54) BLADDER DRAINAGE AID

(75) Inventor: Lennox Hoyte, Tampa, FL (US)

(73) Assignee: University of South Florida, Tampa, FL (US)

( * ) Notice: Subject to any disclaimer, the term of this patent is extended or adjusted under 35 U.S.C. 154(b) by 385 days.

(21) Appl. No.: 12/618,993

(22) Filed: Nov. 16, 2009

(65) Prior Publication Data

US 2010/0063465 A1 Mar. 11, 2010

Related U.S. Application Data

(63) Continuation of application No. PCT/US2008/064072, filed on May 19, 2008.

(60) Provisional application No. 60/938,574, filed on May 17, 2007.

(51) Int. Cl.
*A61F 5/44* (2006.01)

(52) U.S. Cl.
USPC ........... 604/328; 604/329; 604/330; 604/331; 604/274; 604/275; 604/279; 604/544; 604/264; 604/276

(58) Field of Classification Search
USPC ................................................. 604/328–331
See application file for complete search history.

(56) References Cited

U.S. PATENT DOCUMENTS

| | | | |
|---|---|---|---|
| 3,952,729 A * | 4/1976 | Libman et al. ............. | 600/575 |
| 4,946,449 A | 8/1990 | Davis, Jr. | |
| 5,030,199 A | 7/1991 | Barwick et al. | |
| 5,069,663 A | 12/1991 | Sussman | |
| 5,908,403 A | 6/1999 | Bosma et al. | |
| 6,050,934 A | 4/2000 | Mikhail et al. | |
| 6,482,190 B1 | 11/2002 | Genese et al. | |
| 6,673,051 B2 | 1/2004 | Flinchbaugh | |
| 6,814,337 B2 | 11/2004 | Schmaltz | |
| 7,037,303 B2 | 5/2006 | Beaufore et al. | |
| 7,306,586 B2 | 12/2007 | Beaufore et al. | |
| 7,458,957 B2 | 12/2008 | Blake et al. | |
| 2003/0060893 A1 | 3/2003 | Forsell | |
| 2004/0044307 A1 | 3/2004 | Richardson et al. | |
| 2005/0107771 A1 | 5/2005 | Finkbeiner | |
| 2008/0281296 A1 | 11/2008 | Blake et al. | |

OTHER PUBLICATIONS www.visitams.com/about_male_detail_objectname_male_ams_800.html.

* cited by examiner

*Primary Examiner* — Tatyana Zalukaeva
*Assistant Examiner* — Ilya Treyger
(74) *Attorney, Agent, or Firm* — Michele L. Lawson; Smith & Hopen, P.A.

(57) ABSTRACT

Provided is a bladder drainage aid which attaches to the end of Foley Catheter and removes the need for a catheter bag. In a preferred embodiment, the device is a spring-loaded valve with an inflow tube and an outflow tube. The inflow tube connects to the external end of a catheter. The outflow tube can be aimed by the patient. When pressed, the valve opens, allowing the fluid to flow there through. When released, the piston of the valve cuts off fluid flow. The valve cap allows ease of use and the device can be operated with two fingers of one hand. The patient can wear the drainage aid discretely and empty the bladder directly and discretely, such as into a toilet.

6 Claims, 12 Drawing Sheets

BLADDER DRAINAGE AID

CROSS REFERENCE TO RELATED APPLICATIONS

This application claims priority to currently pending PCT Application PCT/US2008/064072 filed May 19, 2008 and U.S. Provisional Patent Application Ser. No. 60/938,574, filed May 17, 2007, the entire contents of which are herby incorporated by reference.

FIELD OF INVENTION

This invention relates to catheters; specifically, drainage valves that attach to the external end of a catheter.

BACKGROUND OF THE INVENTION

Postoperative bladder drainage is currently done using an indwelling bladder catheter attached to a bag for collecting the fluid. After bladder-neck surgeries, the patient is required to wear the bag, sometimes up to three or more weeks. The bag usually is drained at multiple times during the day. Patients often complain about the encumbrance of the bag as well as the associated awkwardness.

SUMMARY OF INVENTION

The present invention provides a bladder drainage aid, which attaches to an existing catheter and negates the need for a catheter bag. The device is small and can be worn discretely, easily fitting into a patient's undergarments. This allows the patient to return quickly to daily activities. The patient can empty the bladder directly and discretely, such as into a toilet. The device can be operated entirely by the use of one hand and requires very low force to start the drainage. This makes the device suitable for elderly patients, and those with limited mobility.

In one embodiment, the device comprises a spring-loaded valve with an inflow tube and an outflow tube. The end of the inflow tube connects to a catheter. The outflow tube, connected to the other side of the valve, can be aimed by the patient. When pressed, the valve opens, allowing fluid to flow from the bladder though the catheter, inflow tube, and valve and out the outflow tube. When released, the piston of the valve cuts off fluid flow, thereby retaining fluid in the bladder. The valve cap allows ease of use and the device can be operated with two fingers of one hand.

In another embodiment, the device comprises a flexible tube, a wheel, and a compression arm. One end of the tube is connected to the end of a catheter. The other end of the tube can be aimed by the patient. The compression arm crimps the tube preventing fluid from passing through. When the wheel is turned, the compression arm lifts away from the tube, allowing it to uncrimp, and fluid passes freely through the device.

In another embodiment, the device comprises a spring-loaded valve. When compressed the valve has a passageway for the external end of a catheter tube to pass through. In this compressed state, fluid can freely pass through the catheter tube. When the valve is released, the passageway loses alignment, thereby crimping the tube and shutting off the flow of fluid through the catheter tube. This embodiment has the added advantage that the fluid flows through the existing catheter tube and does not make contact with the device.

BRIEF DESCRIPTION OF THE DRAWINGS

For a fuller understanding of the invention, reference should be made to the following detailed description, taken in connection with the accompanying drawings, in which:

FIG. 9 is a diagram of an alternate embodiment of the present invention in which a wheel is turned thereby crimping the through-channel and cutting off the flow of fluid from the bladder. The alternate embodiment of the bladder drainage aid is shown encased in a container, which allows access to the wheel, which is rotated by the user to open the valve and allow the passage of fluid there through.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention provides a bladder drainage aid. The device is small and can be worn discretely, easily fitting into a patient's undergarments. This allows the patient to return quickly to daily activities. The patient can empty the bladder directly and discretely, such as into a toilet. The device can be operated entirely by using one hand and requires very low force to start the drainage. This makes the device suitable for elderly patients, and those with limited mobility.

In one embodiment, the invention includes a spring-loaded valve with an inflow tube and an outflow tube. The end of the inflow tube has a beveled tip, sized to plug into a Foley Catheter. The outflow tube connected to the other side of the valve can be aimed by the patient. When pressed, the valve opens allowing fluid to flow from the bladder, through the device, and through the outflow tube. When released, the piston of the valve cuts off fluid flow. The valve cap allows ease of use and the device can be operated with two fingers of one hand.

Figure 1:
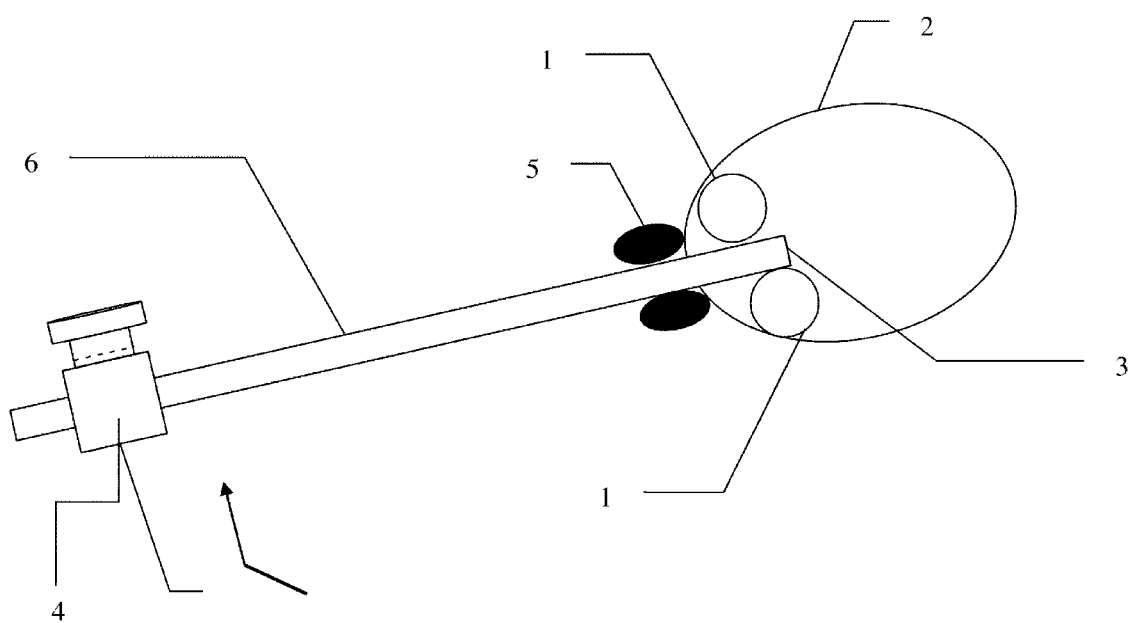
FIG. 1 is a simplified block diagram of a catheter inserted into a bladder with the bladder drainage aid of the present invention affixed to the opposite end.

In one embodiment, the invention is removably attached to the external end of a catheter. FIG. 1 is a simplified diagram showing the placement of catheter tube 6 originating in bladder 2 between two catheter balloons 1, exiting bladder 2 and continuing between two sphincter muscles 5, exiting the body and terminating at the receiving side of the present invention, drainage valve 10. Fluid travels from bladder 2 into catheter tube 6 at urine opening 3, continues through catheter tube 6 to drainage valve 10. Drainage valve 10 controls the flow of fluid passing through catheter tube 6. In its closed state, drainage valve 10 blocks fluid from passing, and in its open state, fluid passes freely through drainage valve 10, emptying bladder 2.

Figure 2:
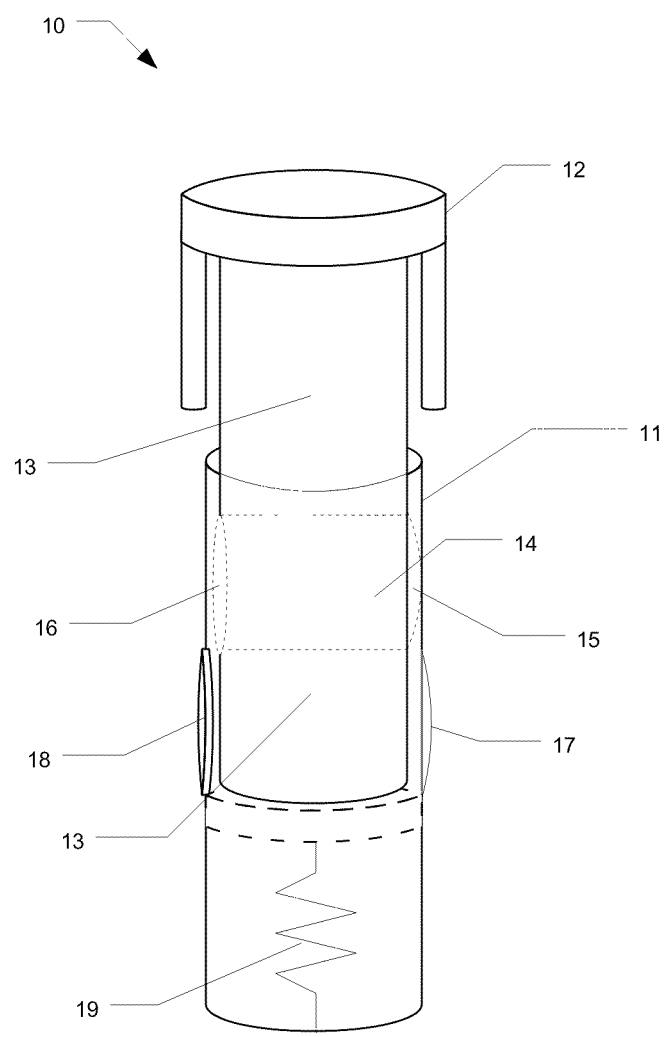
FIG. 2 is a diagram of an embodiment of the present invention, shown in the closed position wherein the flow of fluid from the bladder is cut-off.

In the embodiment, shown in FIG. 2, drainage valve 10 includes a squeezable stopcock comprising valve cap 12, compression spring 19, valve housing 11 having valve inflow opening 17 and valve outflow opening 18, and valve piston 13 having through-channel 14. Through-channel 14 has through-channel inflow opening 15 and through-channel outflow opening 16. In one embodiment, valve inflow opening 17 is adapted to receive the external end of a catheter tube and valve outflow opening 18 is adapted to receive an outflow tube. In another embodiment, shown in FIG. 3, inflow tube 20, adapted to receive the external end of the catheter tube, is attached at valve inflow opening 17 and outflow tube 23 is attached at valve outflow opening 18. Inflow tube 20 is adapted to receive the external end of the catheter tube. Outflow tube 23 is adapted to receive an extension tube or the intake tube of a catheter bag. In this manner, drainage valve 10 can be adapted such that fluid can empty directly from outflow tube 23, into a catheter bag, or in any such manner needed.

Figure 3:
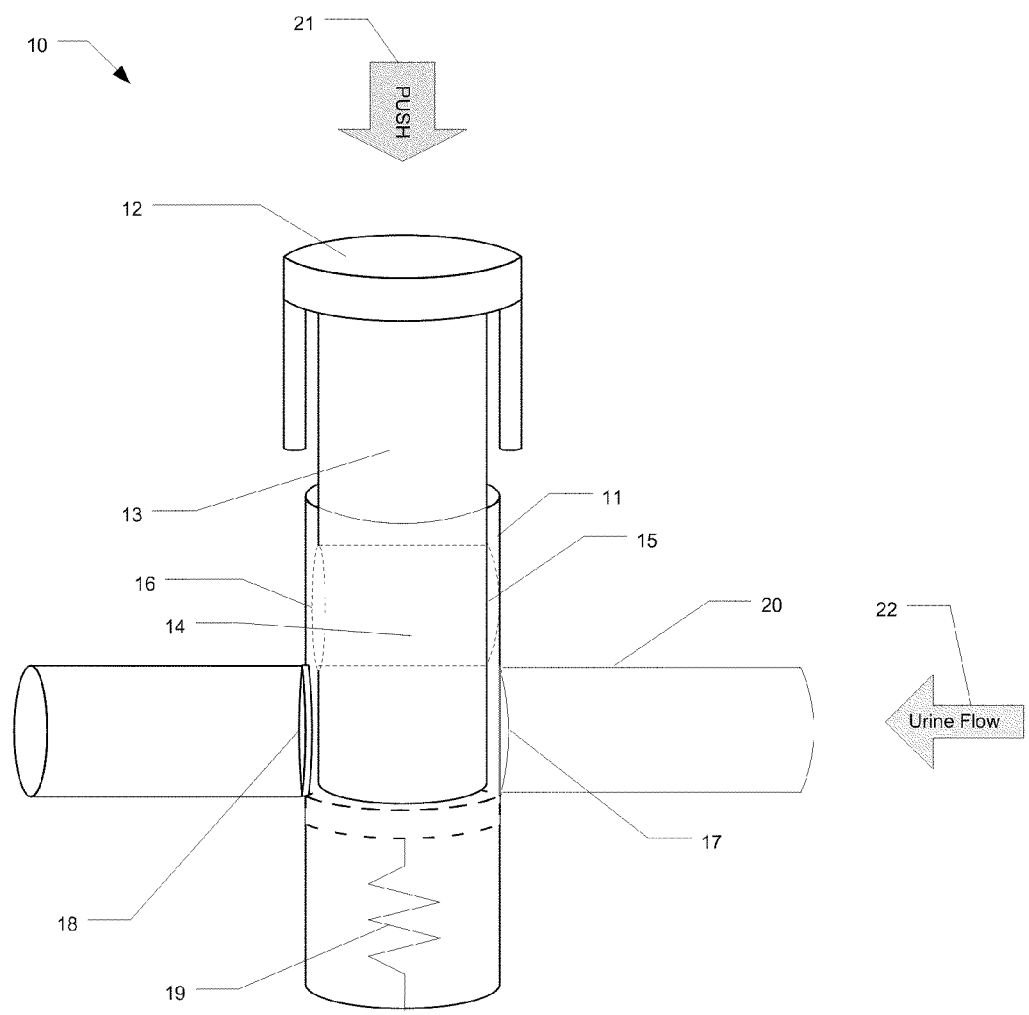
FIG. 3 is a diagram of an embodiment of the present invention in which inflow and outflow tubes are attached. The bladder drainage aid is shown in the closed position wherein the flow of fluid from the bladder is cut-off.

In its closed position, shown in FIGS. 2 and 3, the bladder contents are retained. The solid lower portion of valve piston 13 interrupts fluid 22 flowing from the catheter into valve inflow opening 17. In the closed position, compression spring 19 remains in its extended position.

Figure 4:
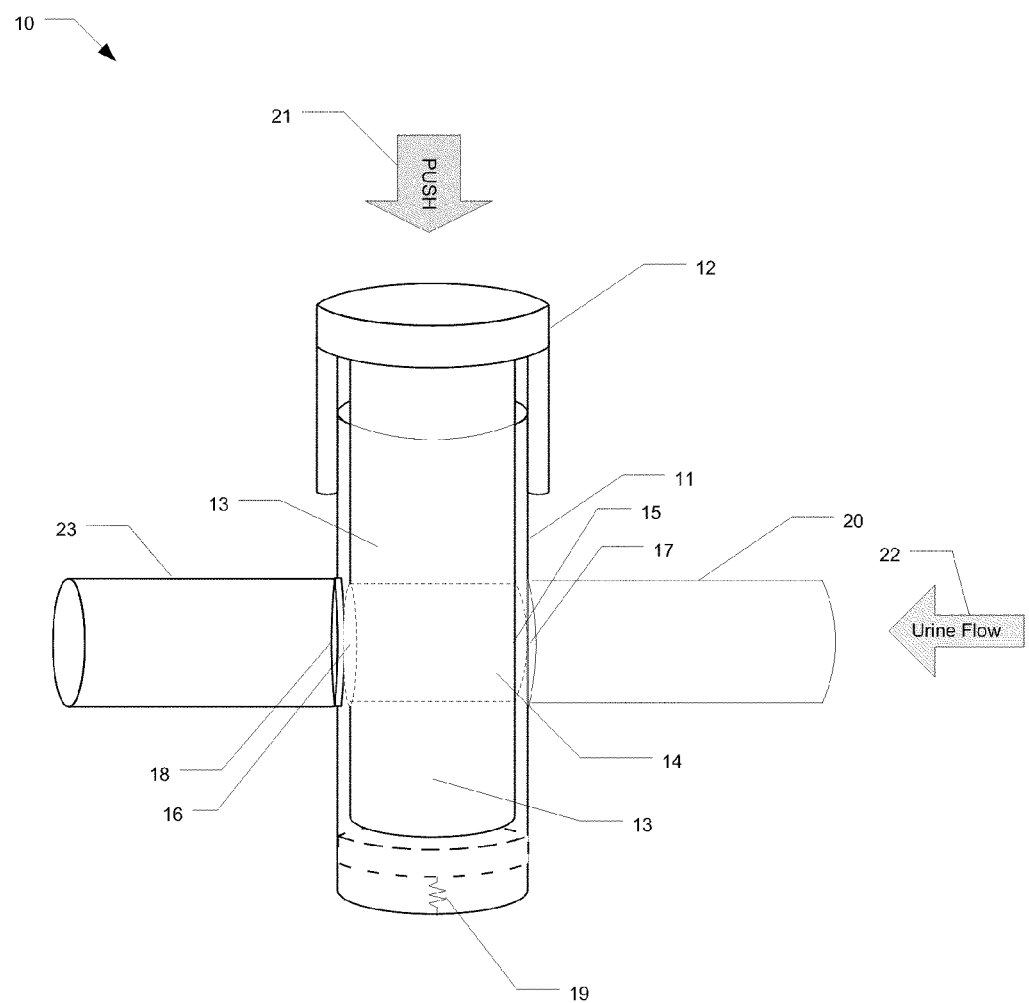
FIG. 4 is a diagram of an embodiment of the present invention in which inflow and outflow tubes are attached. The bladder drainage aid is shown in the open position, wherein the flow of fluid from the bladder is allowed.

As shown in FIG. 4, when valve cap 12 is depressed 21, compression spring 19 is thereby compressed and through-channel 14 of valve piston 13 is lowered until through-channel outflow opening 16 and through-channel inflow opening 15 align with valve outflow opening 18 and valve inflow opening 17. Once alignment occurs, outflow tube 23 is in fluid communication with inflow tube 20.

Figure 5:
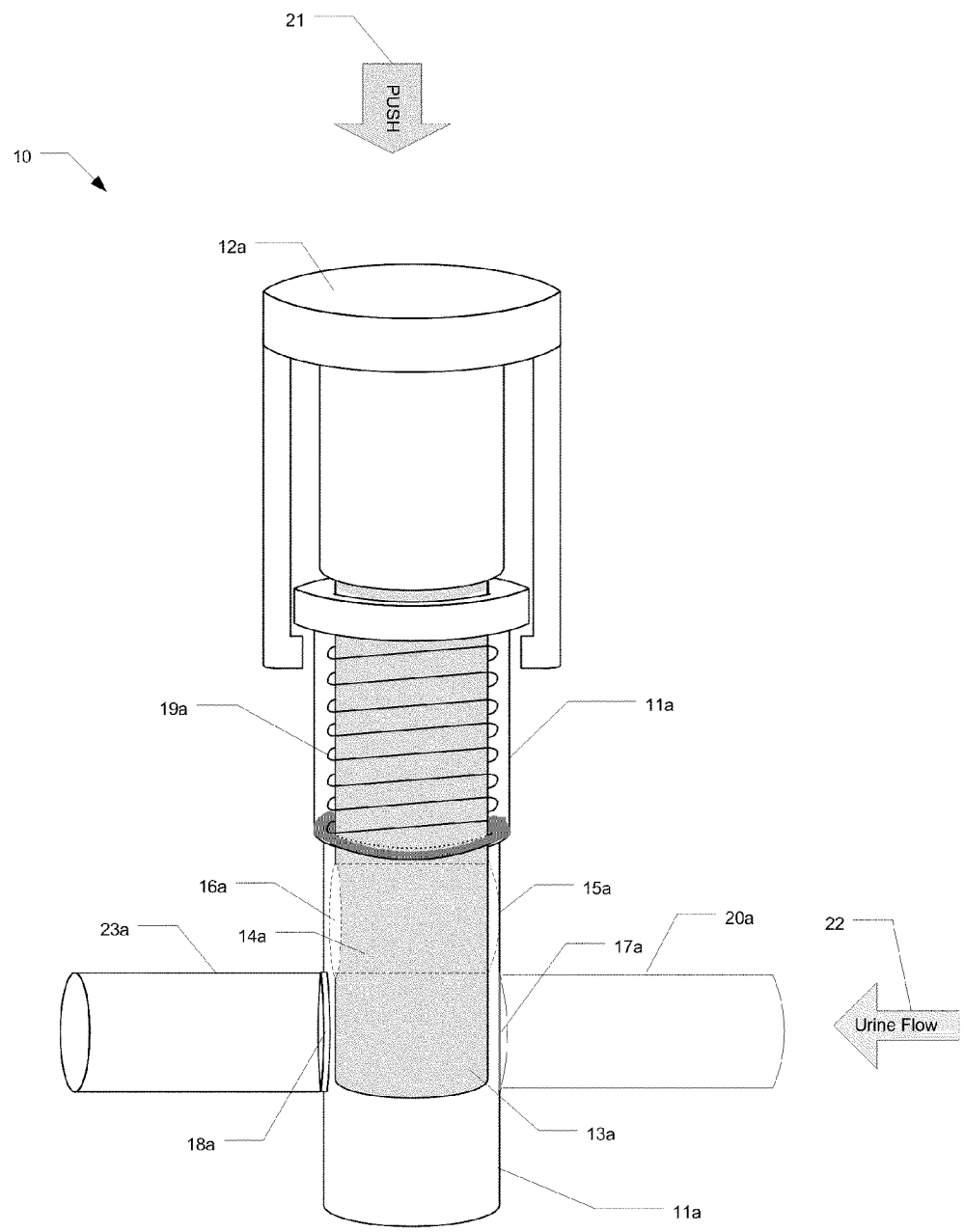
FIG. 5 is a diagram of an alternate embodiment of the present invention in which the spring and valve piston are inverted. The bladder drainage aid is shown in the closed position, wherein the flow of fluid from the bladder is cut-off.
Figure 6:
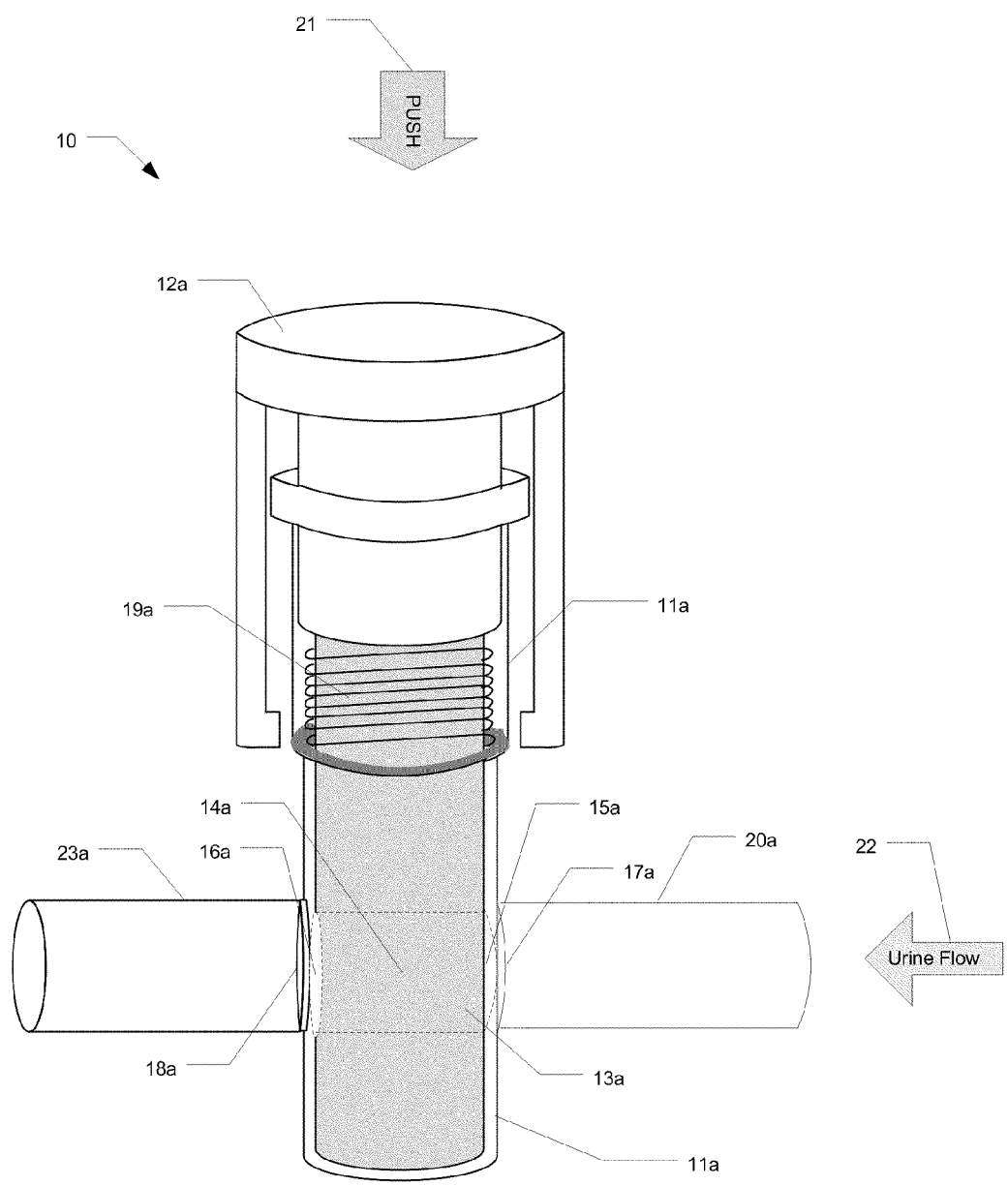
FIG. 6 is a diagram of an alternate embodiment of the present invention in which the spring and valve piston are inverted. The bladder drainage aid is shown in the open position, wherein the flow of fluid from the bladder is allowed.

In another embodiment, shown in FIGS. 5 and 6, drainage valve 10 comprises valve piston 13a with through-channel 14a, valve cap 12a attached to one end of valve piston 13a, compression spring 19a, and valve housing 11a. Valve piston 13a has through-channel 14a with inflow opening 16a and outflow opening 15a. Valve piston 13a is disposed partially inside valve housing 11a. Compression spring 19a is disposed in a position just below valve cap 12a and surrounds a portion of valve piston 13a. Valve housing 11a is comprised of an upper portion and a lower portion. The upper portion has a larger diameter than the lower portion such that compression spring 19a disposed around valve piston 13a will not move to the lower portion of valve housing 11a.

Through-channel 14a is located on valve piston 13a such that, when spring 19a is fully extended, as shown in FIG. 5, the portion of valve piston 13a below through-channel 14a completely blocks valve inflow 17a and valve outflow 18a openings. When valve cap 12a is depressed 21, and spring 19a is thereby compressed, as shown in FIG. 6, through-channel inflow 15a and outflow 16a openings align and are disposed in fluid communication with valve inflow 17a and outflow 18a openings, allowing fluid to flow there through.

Figure 7:
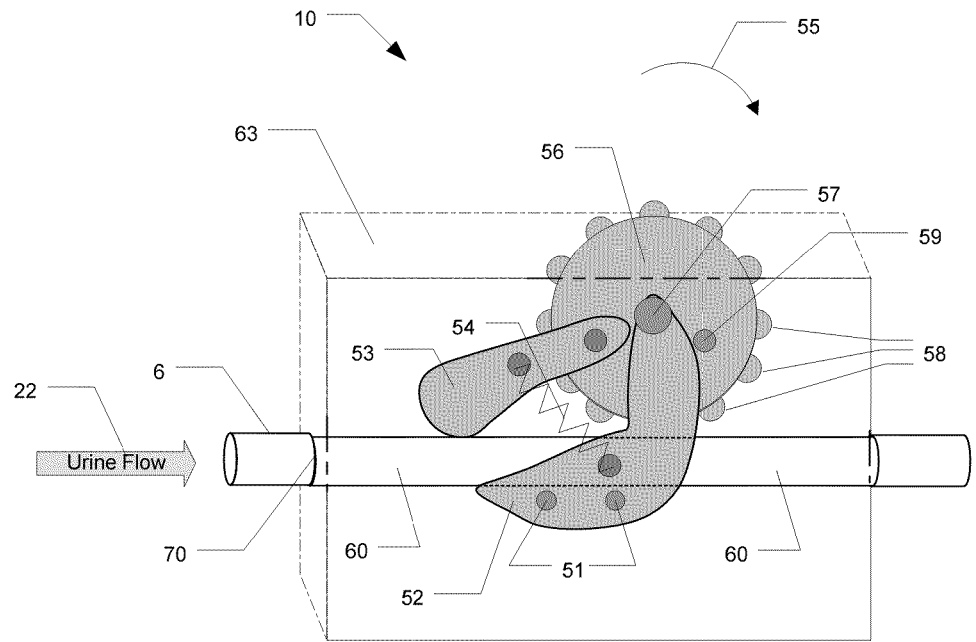
FIG. 7 is a diagram of an alternate embodiment of the present invention in which a wheel is turned, thereby crimping the through-channel and cutting off the flow of fluid from the bladder. The alternate embodiment of the bladder drainage aid is shown in the open position, wherein the flow of fluid from the bladder is allowed.
Figure 8:
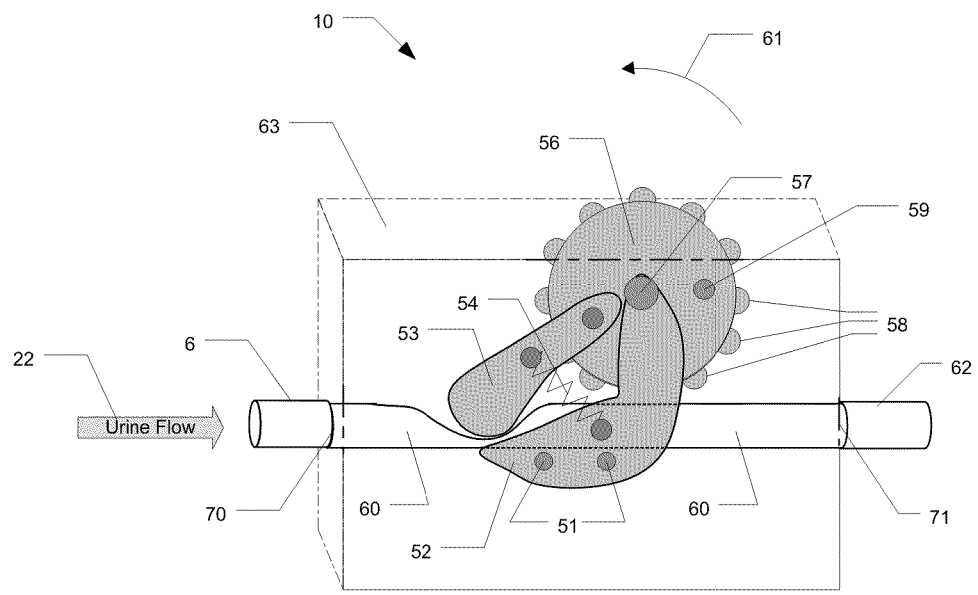
FIG. 8 is a diagram of an alternate embodiment of the present invention in which a wheel is turned thereby crimping the through-channel and cutting off the flow of fluid from the bladder. The alternate embodiment of the bladder drainage aid is shown in the closed position, wherein the flow of fluid from the bladder is cut-off.
Figure 9:
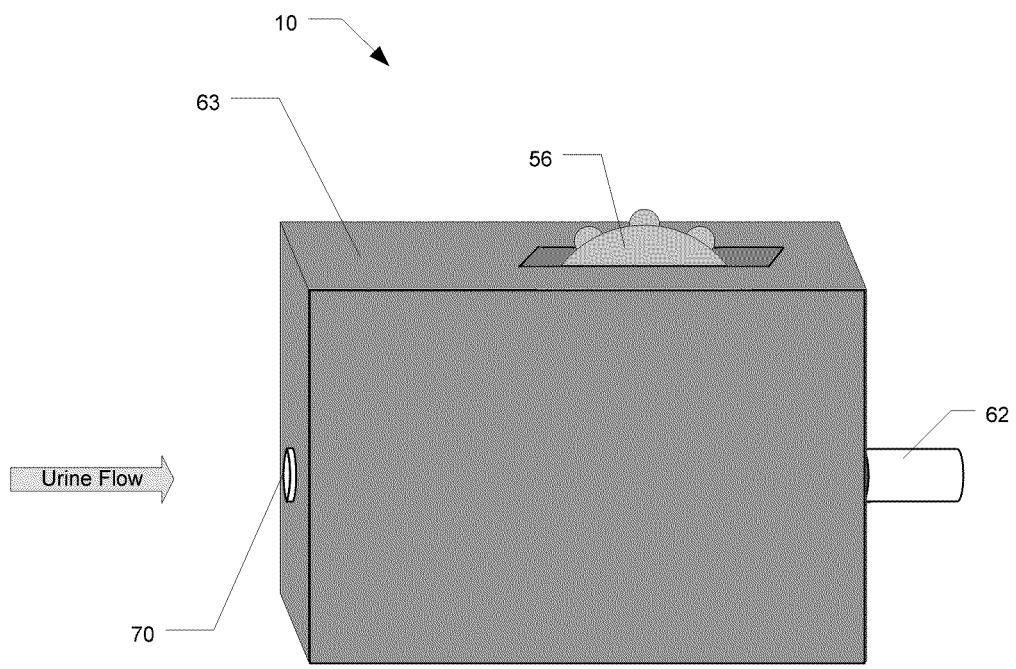

In another embodiment, shown in FIGS. 7, 8, and 9, drainage valve comprises tension spring 54, lower arm 52 having through-channel supports 51, upper arm 53, wheel 56 having multiple knobs 58 on its perimeter, stopper 59, and center axis 57, and flexible through-channel 60 having through-channel inflow opening 70 and through-channel outflow opening 71. Through-channel inflow opening 70 is adapted to receive the external end of catheter tube 6 and through-channel outflow opening 71 is adapted to receive outflow tube 62.

Through-channel 60 is threaded between upper arm 53 and lower arm 52 and one end of tension spring 54 is attached to each arm. Through-channel supports 51 hold through-channel 60 in place. Upper arm 53 is fixedly attached to wheel 56 and lower arm 52 is attached to wheel's center axis 57.

In the natural, closed position of drainage aid 10, shown in FIG. 8, the tension in tension spring 54 pulls upper arm 53 to lower arm 52, crimping flexible through-channel 60 located between the two. By crimping through-channel 60, fluid flow 22 from catheter tube 6 into through-channel 60 is blocked and bladder contents are retained.

To release the bladder contents, the user rotates 55 wheel 56, which, in turn, raises upper arm 53, thereby uncrimping through-channel 60. The bladder contents can then freely pass through the remainder of through-channel 60 and out outflow tube 62. The open position of this embodiment of drainage aid 10 is shown in FIG. 7. Stopper 59 prevents over-rotation of wheel 56 by preventing further rotation of wheel 56 once it encounters lower arm 58. Once bladder contents have been released, the user then simply releases wheel 56. Wheel 56 then rotates in reverse direction 61 due to the compression of tension spring 54. As wheel rotates 56 in reverse direction 61, upper arm 53 is pulled down, crimping through-channel 60 and returning drainage aid 10 to its closed position.

FIG. 9 shows the embodiment of FIGS. 7 and 8 enclosed in container 63 such that wheel 56, through-channel inflow opening 70, and outflow tube 62 are still accessible to the user.

Figure 10A:
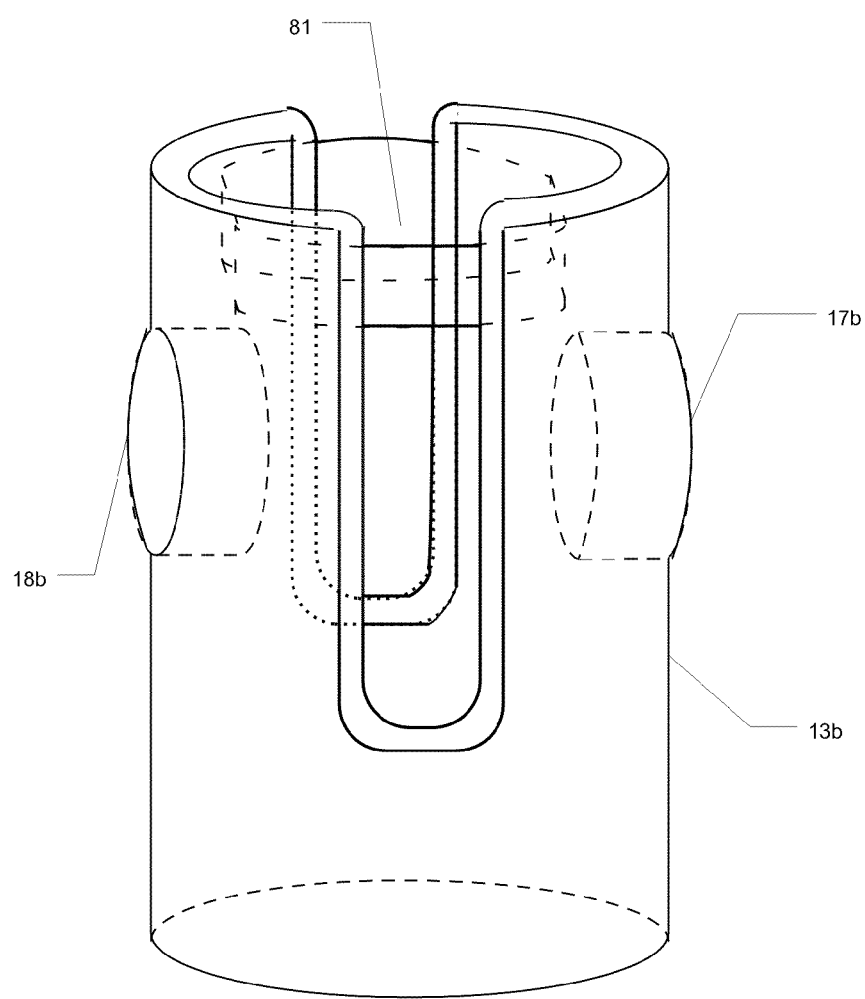
FIG. 10 is a diagram of an alternate embodiment of the present invention in which the external end of a catheter tube is threaded through a compressed valve. In the compressed state, fluid flows freely through the tube, but when the valve is released, the tube is crimped, preventing the flow of fluid through the tube. The alternate embodiment of the bladder drainage aid is shown in its two component pieces.
Figure 10B:
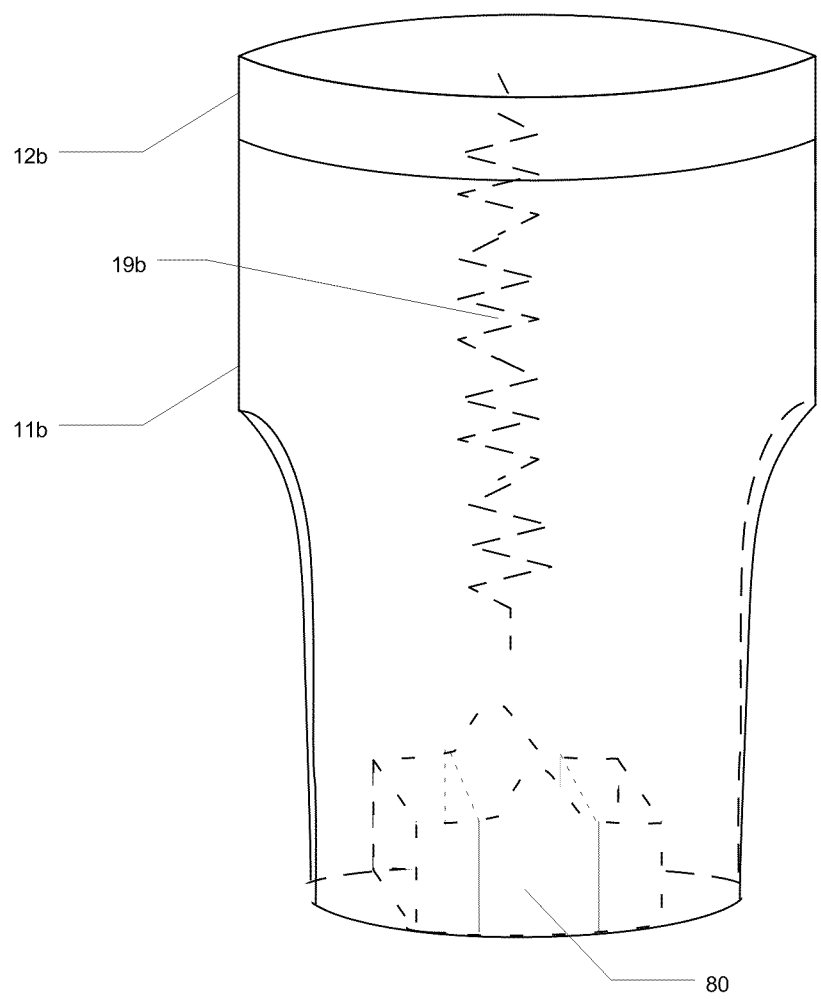
Figure 11:
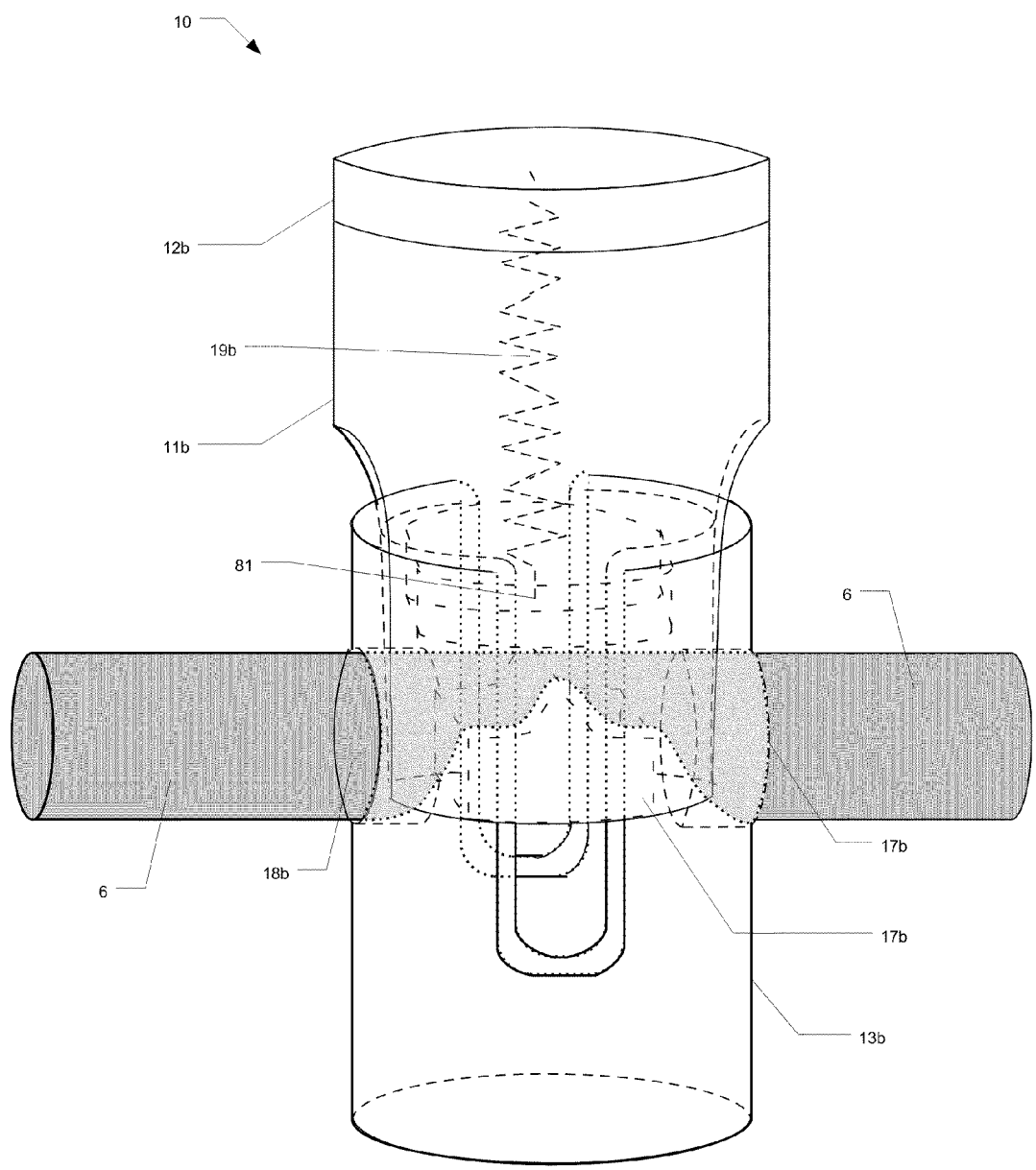
FIG. 11 is a diagram of an alternate embodiment of the present invention in which the external end of a catheter tube is threaded through a compressed valve. The alternate embodiment of the bladder drainage aid is shown in its compressed state, in which fluid flows freely through the tube.
Figure 12:
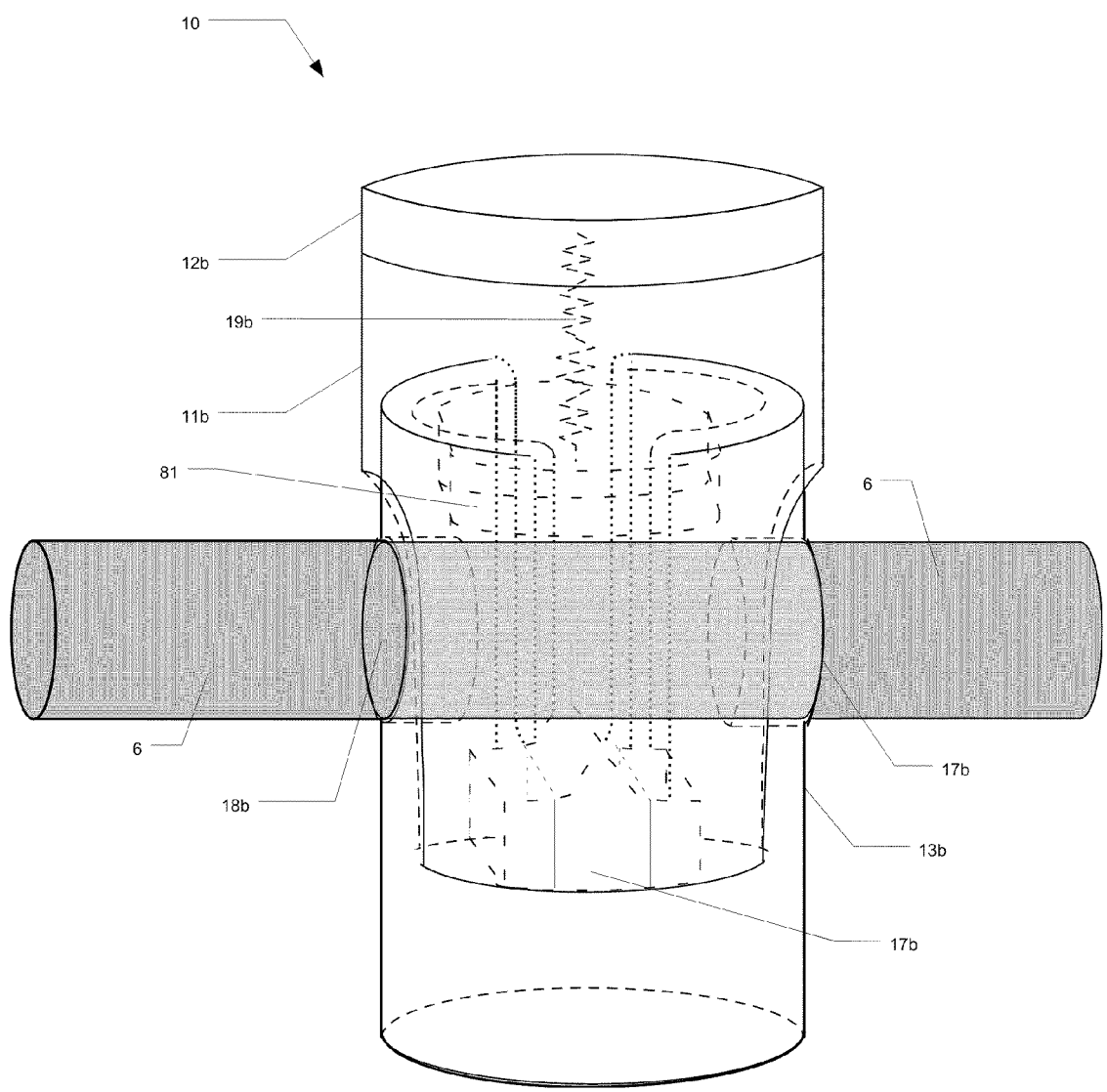
FIG. 12 is a diagram of an alternate embodiment of the present invention in which the external end of a catheter tube is threaded through a compressed valve. The alternate embodiment of the bladder drainage aid is shown in its uncompressed state, in which the tube is crimped, preventing the flow of fluid through the tube.

In another embodiment, shown in FIGS. 10 through 12, drainage valve 10 comprises valve piston 13b and valve housing 11b. Valve piston 13b, shown in FIG. 10A has valve inflow opening 17b, valve outflow opening 18b, and spring base 81. Valve housing 11b, shown in FIG. 10B, has valve cap 12b disposed at one end of valve housing 11b, compression spring 19b, and constricting bar 80. As shown in FIG. 11, valve piston 13b is partially disposed within valve housing 11b. Compression spring 19b, that is disposed within valve housing 11b, connects to valve housing 11b and spring base 81. This embodiment has the added advantage of having fluid flow through the tube and never contacting the device.

When this embodiment of drainage valve 10 is compressed, as shown in FIG. 12, catheter tube 6 is passed into valve inflow opening 17b through the hollow centers of valve piston 13b and valve housing 11b and out of valve outflow opening 18b.

When drainage valve 10 is released, catheter tube 6 is crimped by constricting bar 80, as shown in FIG. 11, thereby preventing fluid from passing out of drainage valve 10. When drainage valve 10 is compressed, constricting bar 80 lowers, catheter tube 6 uncrimps, and fluid can pass freely through drainage valve 10.

Additional elements that can be added to the bladder drainage aid include a pressure sensor which can be embedded within the valve. The sensor is adapted to detect pressure in the catheter when the patient is ambulating. Further, electronics can be added to measure flow pressure or rate while voiding the bladder or to record frequency. The device can be hardwired or employ wireless protocols, i.e. Bluetooth™ to communicate with recording devices or monitors.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A drainage device, comprising:
    a substantially hollow outer cylinder having at least a first side and a second side;
    a first opening disposed in the first side of the outer cylinder;
    an inlet tube disposed in fluid communication with the first opening;
    a second opening disposed in the second side of the outer cylinder;
    an outlet tube disposed in fluid communication with the second opening;
    a valve piston, disposed within the outer cylinder and moveable between a first position and a second position;
    a biasing means disposed between the a valve piston and the outer cylinder, whereby the biasing means biases the inner cylinder into the second position; and
    a through-channel disposed within the valve piston wherein the through-channel is oriented perpendicular to the longitudinal axis of the valve piston;
    wherein the through-channel is in fluid communication with the first opening and the second opening disposed on the sides of the outer cylinder when the a valve piston is in the first position; and
    wherein the through-channel is occluded by the outer cylinder when the inner cylinder is in the second position.

2. The drainage device of claim 1, wherein the biasing means is a compression spring.

3. The drainage device of claim 2,
    wherein the a valve piston and outer cylinder further comprise a first end and a second end;
    wherein the outer cylinder is open at its first end and closed at its second end;
    wherein the second end of the a valve piston is disposed within the outer cylinder; and
    wherein the biasing means is disposed between the second end of the outer cylinder and the second end of the a valve piston.

4. The drainage device of claim 2, wherein the a valve piston and outer cylinder further comprise a first end and a second end;
    wherein the outer cylinder is open at its first end and closed at its second end;
    wherein the second end of the a valve piston is disposed within the outer cylinder; and
    wherein the biasing means is disposed around the a valve piston between the through channel and the first end of the outer cylinder.

5. The drainage device of claim 1, wherein the inlet tube is a catheter removably connected to the outer cylinder.

6. The drainage device of claim 1, wherein the inlet tube is fixedly connected to the outer cylinder at a first end and adapted to receive a catheter at a second end.

* * * * *